United States Patent [19]

Jones et al.

[11] Patent Number: 4,748,165
[45] Date of Patent: May 31, 1988

[54] AMIDINE DERIVATIVES

[75] Inventors: Derrick F. Jones, Macclesfield; Keith Oldham, Cheadle, both of United Kingdom

[73] Assignee: Imperial Chemical Industries PLC, London, England

[21] Appl. No.: 377,137

[22] Filed: May 11, 1982

[30] Foreign Application Priority Data

May 18, 1981 [GB] United Kingdom ............... 8115156

[51] Int. Cl.$^4$ .................. A61K 31/505; C07D 239/42
[52] U.S. Cl. .................................. 514/256; 514/245; 514/247; 514/252; 514/269; 514/333; 544/182; 544/211; 544/212; 544/238; 544/239; 544/240; 544/241; 544/284; 544/296; 544/298; 544/311; 544/326; 544/327; 544/328; 544/329; 544/330; 544/336; 546/261; 546/264; 546/290; 546/296; 546/297; 546/306; 548/127; 548/128; 548/131; 548/134; 548/136; 548/143; 548/202; 248/203; 548/204; 548/205; 548/252; 548/255; 548/263; 548/264; 548/265; 548/266; 548/269; 548/329; 548/376; 548/378
[58] Field of Search ............... 544/211, 330, 336, 212, 544/298, 238, 319, 239, 326, 240, 327, 241, 328, 296, 329; 424/251; 546/261, 264, 290, 296–297; 514/245, 252, 269, 256, 247, 333, 348, 349

[56] References Cited

U.S. PATENT DOCUMENTS

| | | | |
|---|---|---|---|
| 4,165,377 | 8/1979 | Jones et al. | 548/337 |
| 4,165,378 | 8/1979 | Gilman et al. | 424/270 |
| 4,242,350 | 12/1980 | Yellin et al. | 424/270 |
| 4,242,351 | 12/1980 | Yellin et al. | 424/272 |
| 4,252,819 | 2/1981 | Hirata et al. | 424/285 |
| 4,362,728 | 12/1982 | Yellin et al. | 424/249 |

FOREIGN PATENT DOCUMENTS

| | | |
|---|---|---|
| 866155 | 4/1977 | Belgium . |
| 35228 | 9/1981 | European Pat. Off. . |
| 50407 | 4/1982 | European Pat. Off. . |
| 55-115877 | 2/1979 | Japan . |
| 55-115860 | 3/1979 | Japan . |
| 57026663 | 7/1980 | Japan . |
| 57026674 | 7/1980 | Japan . |
| 57026675 | 7/1980 | Japan . |
| 56-055383 | 5/1981 | Japan . |
| 56-122368 | 9/1981 | Japan . |
| 2003471 | 3/1979 | United Kingdom . |
| 2052478A | 1/1981 | United Kingdom . |
| 2055800A | 3/1981 | United Kingdom . |
| 2085871 | 5/1982 | United Kingdom . |

Primary Examiner—Glennon H. Hollrah
Assistant Examiner—James H. Turnipseed
Attorney, Agent, or Firm—Cushman, Darby & Cushman

[57] ABSTRACT

This invention relates to amidine derivatives which are histamine H-2 antagonists and which inhibit gastric acid secretion. According to the invention there is provided a guanidine derivative of the formula I:

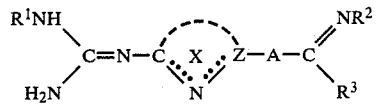

in which $R^1$ is hydrogen or a 1–10C alkyl, 3–8C cycloalkyl, 4–14C cycloalkylalkyl, 3–6C alkenyl, 3–6C alkynyl, 1–6C alkanoyl, 6–10C aryl, 7–11C aralkyl or 7–11C aroyl radical, the latter three being optionally substituted; ring X is a heterocyclic ring as defined in the specification; A is phenylene or 5–7C cycloalkylene or a 1–8C alkylene chain into which is optionally inserted one or two groups; and $R^2$ and $R^3$ are a variety of radicals described in the specification: and the pharmaceutically-acceptable acid-addition salts thereof. Manufacturing processes and pharmaceutical compositions are also described.

17 Claims, No Drawings

AMIDINE DERIVATIVES

This invention relates to amidine derivatives which are histamine H-2 antagonists and which inhibit gastric acid secretion.

It is postulated that the physiologically-active compound histamine, which occurs naturally within the animal body, is able to combine, in the course of exerting its activity, with certain specific receptors of which there are at least two distinct and separate types. The first has been named the H-1 receptor (Ash and Schild, *Brit. J. Pharmac.* 1966, 27, 427) and the action of histamine at this receptor is blocked (antagonised) by classical "antihistamine" drugs such as mepyramine. The second histamine receptor has been named the H-2 receptor (Black et al., *Nature*, 1972, 236, 385) and the action of histamine at this receptor is blocked by drugs such as cimetidine. It is known that one of the results of the blockade of the action of histamine at the H-2 receptor is the inhibition of the secretion of gastric acid and a compound which possesses this ability is therefore useful in the treatment of peptic ulcers and other conditions caused or exacerbated by gastric acidity.

In UK Patent Applications Nos. GB2052478A and GB2055800A there are described histamine H-2 receptor antagonists which are 2-guanidinothiazole derivatives carrying a side chain in the 4-position to the end of which is attached a substituted amidine group. It has now been discovered that if the thiazole ring is replaced by one of a variety of 5- and 6-membered heterocycles, there are obtained potent histamine H-2 receptor antagonists.

According to the invention there is provided a guanidine derivative of the formula I:

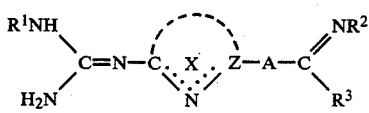

in which $R^1$ is a hydrogen atom or a 1–10C alkyl, 3–8C cycloalkyl, 4–14C cycloalkylalkyl, 3–6C alkenyl, 3–6C alkynyl, 1–6C alkanoyl, 6–10C aryl, 7–11C aralkyl or 7–11C aroyl radical, the aryl, aralkyl and aroyl radicals being optionally substituted on the aryl ring by one or two substituents selected from halogen atoms and 1–6C alkyl, 1–6C alkoxy, 1–6C alkylthio, trifluoromethyl, hydroxy and amino radicals; in ring X the dotted line is a double bond on one side of the nitrogen atom and Z is a carbon or nitrogen atom such that ring X is a 1,2,3-triazole, 1,2,4-triazole, pyrazole, pyrazine, pyridine, pyrimidine or 1,3,5-triazine ring, which ring may, where possible, carry one or two optional substituents, the optional substituents on ring X being selected from fluorine, chlorine and bromine atoms and 1–6C alkyl, 1–6C alkoxy, trifluoromethyl, hydroxy and amino radicals; A is a phenylene or a 5–7C cycloalkylene radical or a 1–8C alkylene chain which is optionally substituted by one or two 1–3C alkyl radicals and into which is optionally inserted, as part of the backbone of the chain, one or two groups selected from oxygen and sulphur atoms and NH, 1–6C N-alkyl, cis and trans vinylene, ethynylene, phenylene and 5–7C cycloalkylene radicals, provided that the shortest link between ring X and $C(R^3)=NR^2$ is of at least 3 atoms, provided that when an optional insertion is made in chain A which results in the inserted group being directly attached to $C(R^3)=NR^2$ the inserted group is other than an NH or N-alkyl radical, and provided that no two insertions selected from oxygen and sulphur atoms and NH and N-alkyl radicals are directly attached one to the other; $R^2$ is a hydrogen atom or a 1–6C alkyl, 3–8C cycloalkyl, 4–14C cycloalkylalkyl, 1–6C haloalkyl, 1–6C hydroxyalkyl, 1–6C aminoalkyl, 2–10C alkylaminoalkyl, 3–14C dialkylaminoalkyl, 2–6C carboxyalkyl, 1–6C alkanoyl, 7–11C aroyl, 6–10C aryl, 7–11C arylalkyl, 2–6C alkenyl, 2–6C alkynyl, 2–6C haloalkanoyl, 1–6C thioalkanoyl, 7–11C thioaroyl, cyano, carbamoyl, thiocarbamoyl, 2–6C alkylcarbamoyl, 3–10C dialkylcarbamoyl, 2–6C alkylthiocarbamoyl, 3–10C dialkylthiocarbamoyl, carboxy, 2–6C alkoxycarbonyl, 2–6C alkoxythiocarbonyl, oxamoyl, sulphamoyl, 1–6C alkylsulphamoyl, 2–10C dialkylsulphamoyl, 6–10C arylsulphamoyl, 7–11C aralkylsulphamoyl, 1–6C alkanesulphonyl, 6–10C arenesulphonyl, hydroxy, 1–6C alkoxy, amino, 1–6C alkylamino, 2–10C dialkylamino, 6–10C arylamino, 2–6C alkoxycarbonylamino, 7–11C aryloxycarbonylamino, 1–6C alkanoylamino, 7–11C aroylamino, 1–6C thioalkanoylamino, 7–11C thioaroylamino, heteroarylcarbonylamino, heteroaryl-(1–6C)alkylcarbonylamino, 1–6C alkanesulphonylamino, 6–10C arenesulphonylamino, ureido, thioureido, oxamoylamino, heteroaryl or heteroaryl-(1–6C)alkyl radical; $R^3$ is a radical of the formula $HNR^4$ in which $R^4$ is a hydrogen atom or a 1–6C alkyl, 2–6C alkenyl, 2–6C alkynyl, cyano, 1–6C alkanoyl, carbamoyl, 2–6C alkylcarbamoyl or 1–6C alkanoylamino radical; or $R^2$ and $R^4$ are joined to form, together with the N—C=N chain to which they are attached, a monocyclic or bicyclic heterocyclic ring system composed of 5- and/or 6- membered rings, which ring system may be partially unsaturated or fully unsaturated, which ring system may optionally include additional hetero atoms selected from oxygen, nitrogen and sulphur atoms and which ring system may, where possible, carry one, two or three optional substituents selected from fluorine, chlorine and bromine atoms and 1–6C alkyl, 1–6C alkoxy, 1–6C alkylthio, trifluoromethyl, hydroxy, amino, 6–10C aryl, 7–11C arylalkyl, carboxy, 2–6C carboxyalkyl, 2–6C alkoxycarbonyl, 3–10C alkoxycarbonylalkyl, 1–6C hydroxyalkyl, heteroaryl-(1–6C)alkyl, furyl, thienyl, pyrrolyl, thiazolyl, oxazolyl, imidazolyl, thiadiazolyl, oxadiazolyl, triazolyl, pyrazolyl and pyrimidyl radicals; or $R^2$ is a hydrogen atom or a 1–6C alkyl, 2–6C alkenyl or 2–6C alkynyl radical and $R^3$ is a carboxy radical; and wherein when $R^2$ is or contains a heteroaryl radical and when $R^2$ and $R^4$, when joined, is substituted by a heteroarylalkyl radical, that heteroaryl radical is a 5- or 6- membered heterocyclic ring which contains 1, 2, 3 or 4 heteroatoms selected from oxygen, nitrogen and sulphur atoms, such ring being optionally substituted by one or two substituents selected from methyl and amino radicals; or $R^2$ and $R^4$ are joined to form, together with the N—C=N chain to which they are attached, a ring of the formula II:

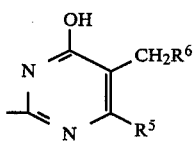

in which $R^5$ is a hydrogen atom or a 1–4C alkyl radical and $R^6$ is a furan-2-yl or thien-2-yl radical substituted in the 5-position, a phenyl radical substituted in the 3- or 4-position, a pyrid-3-yl radical substituted in the 5- or 6-position, a pyrid-4-yl radical substituted in the 2-position, or a pyrid-2-yl radical substituted in the 4- or 5-position, the substituent on R⁶ being a radical of the formula III:

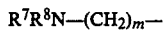

in which R⁷ and R⁸ are 1–4C alkyl radicals or R⁷ and R⁸ are joined to form, together with the nitrogen atom to which they are attached, a pyrrolidine, piperidine or morpholine ring and m is 1 to 4:

and the pharmaceutically-acceptable acid-addition salts thereof.

It is to be understood that, in the above formula I and throughout this specification, although the double bonds in both groups attached to ring X have been inserted in particular positions, other tautomeric forms are possible, and this invention includes such tautomeric forms within its scope, both in terms of the compounds of the invention and in terms of the manufacturing processes. Similarly, when R² and R⁴ are joined to form a heterocyclic ring which is substituted by a hydroxy radical, that radical may exist in the tautomeric keto form. It is also to be understood that when A is or contains a cycloalkylene radical the groups attached to this radical may be in the cis or trans configuration. When A is or contains a cycloalkylene radical and/or when A is an alkylene chain substituted by one or two alkyl radicals, the compound of the formula I will, in most instances, contain at least one asymmetric centre. In such cases the compound of the formula I will therefore exist in at least two enantiomeric forms, the precise number being determined by the number of asymmetric centres. The biological activity, as hereinafter defined, of these enantiomeric forms may differ, and it is therefore to be understood that this invention encompasses the racemate of the formula I, including any possible diastereoisomeric forms, and any enantiomeric form which possesses the disclosed biological activity, it being a matter of common general knowledge to one skilled in the art how to separate diastereoisomeric forms and how to separate a racemate into its enantiomers and determine the biological activity of each.

A particular value for R¹ is a hydrogen atom or a methyl, ethyl, propyl, isopropyl, butyl, cyclohexyl, cyclohexylmethyl, allyl, propargyl, acetyl, phenyl, benzyl or benzoyl radical, the phenyl, benzyl and benzoyl radicals being optionally substituted on the benzene ring by one or two substituents selected from fluorine, chlorine and bromine atoms and methyl, methoxy, methylthio, trifluoromethyl, hydroxy and amino radicals.

A particular value for the optional substituent on ring X is one or two substituents selected from fluorine, chlorine and bromine atoms and methyl, methoxy, trifluoromethyl, hydroxy and amino radicals.

A particular value for —A— is a phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethioethylene, methylenethioethylene, methylenethiopropylene, methyleneoxymethylene, methyleneoxyethylene, ethyleneoxyethylene, oxy-2-methylethylene, thiopropylenethiomethylene, oxypropyleneoxy, oxyethyleneoxymethylene, oxyethylenethio, oxypropylenethio, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethylene-ethynylenemethylene radical. These values for —A— are written reading from left to right in formula I such that the first named part of the radical is attached to ring X and the last named part of the radical is attached to C(R³)=NR². Thus, for example, when —A— is a thiotrimethylene radical, the compound of the formula I contains the part structure IV:

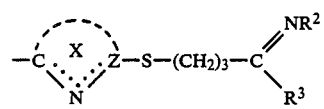

A particular value for R² is a hydrogen atom or a methyl, cyclohexyl, cyclobutylmethyl, 2,2,2-trifluoroethyl, 2-hydroxyethyl, 2-aminoethyl, 2-methylaminoethyl, 2-dimethylaminoethyl, 2-carboxyethyl, acetyl, benzoyl, phenyl, benzyl, allyl, propargyl, trifluoroacetyl, thioacetyl, thiobenzoyl, cyano, carbamoyl, thiocarbamoyl, methylcarbamoyl, dimethylcarbamoyl, methylthiocarbamoyl, dimethylthiocarbamoyl, carboxy, methoxycarbonyl, methoxythiocarbonyl, oxamoyl, sulphamoyl, methylsulphamoyl, dimethylsulphamoyl, phenylsulphamoyl, benzylsulphamoyl, methanesulphonyl, benzenesulphonyl, hydroxy, methoxy, amino, methylamino, dimethylamino, phenylamino, methoxycarbonylamino, phenoxycarbonylamino, acetylamino, benzoylamino, thioacetylamino, thiobenzoylamino, heteroarylcarbonylamino, heteroarylacetylamino, methanesulphonylamino, benzenesulphonylamino, ureido, thioureido, oxamoylamino, heteroaryl or heteroarylmethyl radical wherein the heteroaryl part is a furyl, thienyl, pyrrolyl, thiazolyl, oxazolyl, imidazolyl, thiadiazolyl, oxadiazolyl, triazolyl, pyrazolyl, pyridyl or pyrimidyl radical which is optionally substituted by one or two substituents selected from methyl and amino radicals.

A particular value for R³ is a radical of the formula NHR⁴ in which R⁴ is a hydrogen atom or a methyl, allyl, propargyl, cyano, acetyl, carbamoyl, methylcarbamoyl or acetylamino radical. A further particular value for R³ is a carboxy radical when R² is a hydrogen atom or a methyl, allyl or propargyl radical.

A particular value for the ring system formed when R² and R⁴ are joined is an imidazole, imidazoline, triazole, pyrimidine, oxadiazole, thiadiazole, 1,3,5-triazine, 1,2,4-triazine, benzimidazole, quinazoline or purine (linked through the 2- or 8- position) ring system each of which ring systems may, where possible, carry one, two or three optional substituents selected from fluorine, chlorine and bromine atoms and methyl, ethyl, propyl, butyl, methoxy, methylthio, trifluoromethyl, hydroxy, amino, phenyl, benzyl, carboxymethyl, methoxycarbonyl, methoxycarbonylmethyl, hydroxymethyl, furyl, thienyl, pyrrolyl, thiazolyl, oxazolyl, imidazolyl, thiadiazolyl, oxadiazolyl, triazolyl, pyrazolyl and pyrimidyl radicals and heteroarylmethyl and 2-heteroarylethyl radicals in which the heteroaryl part is a furyl, thienyl, pyrrolyl, thiazolyl, oxazolyl, imidazolyl, thiadiazolyl, oxadiazolyl, triazolyl, pyrazolyl, pyridyl or pyrimidyl radical, each optionally substituted by one or two substituents selected from methyl and amino radicals.

A further particular value for the ring formed when $R^2$ and $R^4$ are joined is a ring of the formula II given above in which $R^5$ is a hydrogen atom or a methyl radical and $R^6$ is a furan-2-yl or thien-2-yl radical substituted in the 5-position, a phenyl radical substituted in the 3- or 4- position, a pyrid-3-yl radical substituted in the 5- or 6-position, a pyrid-4-yl radical substituted in the 2-position or a pyrid-2-yl radical substituted in the 4- or 5-position, the substituent on $R^6$ being a radical of the formula III given above in which $R^7$ and $R^8$ are methyl radicals or are joined to form, together with the nitrogen atom to which they are attached, a pyrrolidine, piperidine or morpholine ring and m is 1 to 4, preferably 1.

The following are eight preferred features of the guanidine derivative of the formula I. When any one of these features is taken, either singly or in combination, with the other general or particular features of the guanidine derivative of the formula I listed above, there are obtained preferred sub-groups of compounds within the above general definition.

1. $R^2$ is a cyano radical and $R^3$ is a radical of the formula $NHR^4$ in which $R^4$ is a hydrogen atom.
2. $R^2$ and $R^4$ are joined to form an optionally-substituted imidazole, triazole or pyrimidine ring.
3. $R^2$ and $R^4$ are joined to form an unsubstituted imidazole ring, a triazole ring substituted in the 5-position by a 1–6C alkyl radical or a pyrimidine ring substituted in the 4-position by a hydroxy radical and in the 5-position by a 1–6C alkyl radical.
4. $R^2$ and $R^4$ are joined to form a triazole ring substituted in the 5-position by a methyl radical or a pyrimidine ring substituted in the 4-position by a hydroxy radical and in the 5-position by a methyl or ethyl radical.
5. $R^1$ is an ethyl or propyl radical.
6. Ring X carries no optional substituent.
7. Ring X is a 1,2,3-triazole, or pyrimidine in which A is linked at the 2-position, ring.
8. —A— is a tetramethylene or thiotrimethylene radical.

Specific compounds of the invention are described in the Examples. The following is a preferred group of compounds:

N-cyano-4-(4-[2-propylguanidino]pyrimid-2-ylthio)-butanamidine (Example 1);
N-cyano-5-(4-[2-propylguanidino]pyrimid-2-yl)valeramidine (Example 2);
5-methyl-3-(3-[4-(2-propylguanidino)pyrimid-2-ylthio]propyl)-1,2,4-triazole (Example 4);
2-[4-(4-[2-propylguanidino]pyrimid-2-yl)butyl]-5-ethyl4-hydroxypyrimidine (Example 5);
2-[4-(4-[2-propylguanidino]pyrimid-2-yl)butyl]-5-methyl-4-hydroxypyrimidine (Example 6);
3-methyl-5-(4-[4-(2-ethylguanidino)-1,2,3-triazol-2-yl]butyl)-1,2,4-triazole (Example 10);
and the pharmaceutically-acceptable acid-addition salts thereof.

Of this group the compounds of Examples 1 and 4 are particularly preferred.

A suitable pharmaceutically-acceptable acid-addition salt of the guanidine derivative of the invention is, for example, a salt formed with hydrochloric, hydrobromic, phosphoric, sulphuric, acetic, citric or maleic acid.

The guanidine derivative of the invention may be manufactured by methods in which the actual chemical reactions involved are known in themselves. The following processes, $R^1$, $R^2$, $R^3$, A and ring X having the meanings stated above, unless indicated otherwise, are therefore provided as further features of the invention.

The process of the invention is characterised by:

(a) for those compounds in which $R^3$ is a radical of the formula $NHR^4$ and $R^2$ and $R^4$ are not joined, reaction of a compound of the formula V:

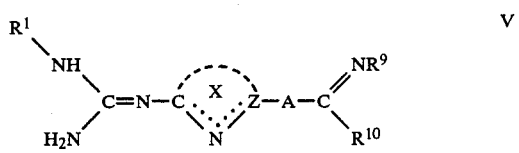

in which $R^9$ has one of the values given above for $R^2$ or $R^4$ and $R^{10}$ is a displaceable radical with a compound of the formula VI:

in which $R^{11}$ has one of the values given above for $R^4$ or $R^2$ respectively. When $R^{11}$ is a hydrogen atom, that is the compound of the formula VI is ammonia, it is convenient to use it in the form of a salt such as ammonium chloride. $R^{10}$ may, for example, be a 1–6C alkoxy radical, for example a methoxy or ethoxy radical. The reaction may be carried out in a diluent or solvent, for example methanol or ethanol. The reaction generally proceeds at ambient temperature, but may, in certain instances, require acceleration or completion by the application of heat, for example by heating to the boiling point of the diluent or solvent.

(b) for those compounds in which $R^3$ is a radical of the formula $NHR^4$ in which $R^2$ and $R^4$ are joined to form a heterocyclic ring system, reaction of a compound of the formula VII:

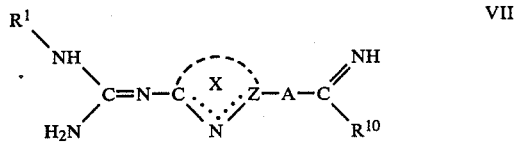

in which $R^{10}$ is a displaceable radical, with a compound containing a 2-, 3- or 4-atom chain, two adjacent members of which may be incorporated into a 5- or 6-membered carbocyclic or heterocyclic ring, and in which the chain is functionalised in such a way that a cyclised amidine is formed. $R^{10}$ may, for example be an amino or 1–6C alkoxy, for example methoxy or ethoxy, radical. The following examples illustrate this general reaction for specific ring systems. When the ring to be formed is an optionally-substituted imidazole ring, the compound of the formula VII in which $R^{10}$ is a displaceable radical is reacted with a compound of the formula VIII:

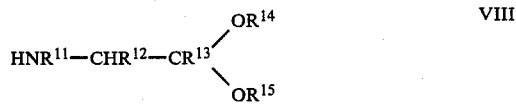

in which $R^{11}$, $R^{12}$ and $R^{13}$ are hydrogen atoms or the optional substituents on the heterocyclic ring system and $R^{14}$ and $R^{15}$ are 1–6C alkyl, for example methyl or ethyl, radicals, or $R^{14}$ and $R^{15}$ are joined to form an ethylene or propylene radical. When the ring to be formed is an optionally-substituted 1-imidazoline ring, the compound of the formula VII in which R¹⁰ is a displaceable radical is reacted with a compound of the formula IX:

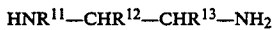

in which R¹¹, R¹² and R¹³ have the meanings given above. When the ring to be formed is an optionally substituted pyrimidine ring which carries a hydroxy radical in the 4-position, the compound of the formula VII in which R¹⁰ is an amino radical is reacted with a compound of the formula X:

in which R¹², R¹³ and R¹⁴ have the meanings given above, for example as illustrated in Examples 5 and 6. When the ring to be formed is a pyrimidine ring which carries an amino radical in the 4-position, the compound of the formula VII in which R¹⁰ is an amino radical is reacted with 2-chloroacrylonitrile. The process of the invention may be conducted in a diluent or solvent, such as methanol or ethanol, and be accelerated or completed by the application of neat, for example by heating to the boiling point of the diluent or solvent. When using the compound of the formula VIII the reaction may conveniently be conducted in two stages, the second stage being initiated by the addition of a mineral acid, for example HCl. When using 2-chloroacrylonitrile as starting material, the reaction may be conducted in the presence of triethylamine.

(c) for those compounds in which R³ is a radical of the formula NHR⁴ in which R² and R⁴ are joined to form a 1,2,4-triazole ring substituted in the 5-position by an alkyl, trifluoromethyl, hydroxy, aryl, arylalkyl, carboxyalkyl, alkoxycarbonylalkyl, hydroxyalkyl, heteroarylalkyl, furyl, thienyl, pyrrolyl, thiazolyl, oxazolyl, imdazolyl, thiadiazolyl, oxadiazolyl, triazolyl, pyrazolyl or pyrimidyl radical, cyclisation of a compound of the formula XI:

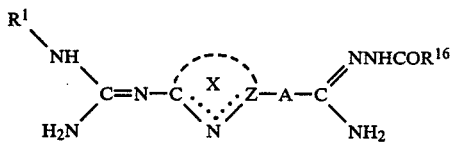

in which R¹⁶ is a 1–6C alkyl, trifluoromethyl, hydroxy, 1–6C alkoxy, 6–10C aryl, 7–11C arylalkyl, 2–6C carboxyalkyl, 2–6C alkoxycarbonyl, 3–10C alkoxycarbonylalkyl, 1–6C hydroxyalkyl, heteroaryl-(1–6C) alkyl, furyl, thienyl, pyrrolyl, thiazolyl, oxazolyl, imidazolyl, thiadiazolyl, oxadiazolyl, triazolyl, pyrazolyl or midyl radical. The process may be carried out by heating the compound of the formula XI in the absence of a diluent or solvent, for example at a temperature of between 50° and 200° C. Alternatively, the process may be conducted in a diluent or solvent, for example ethanol, at the boiling point of the diluent or solvent.

(d) for those compounds in which R² is a carbamoyl radical, hydrolysis of the corresponding compound in which R² is a cyano radical. The process may, for example, be carried out in an alcoholic diluent or solvent such as methanol or ethanol, or mixtures of these with chloroform, containing dissolved HCl gas, and in the presence of at least one equivalent of water.

(e) for those compounds in which the group inserted into A is an oxygen or sulphur atom or an NH or N-alkyl radical, reaction of a compound of the formula XII or XIII:

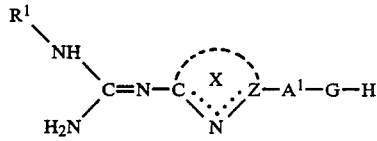

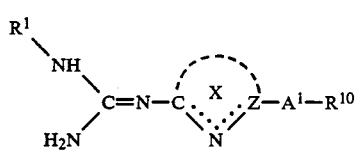

with a compound of the formula XIV or XV respectively:

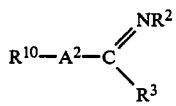

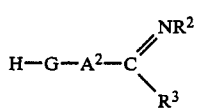

in which G is an oxygen or sulphur atom or an NH or N-alkyl radical, R¹⁰ is a displaceable radical and A¹ and A² are fragments of A, including direct bonds, and are such that A¹—G—A² falls within the general definition of A given above. R¹⁰ is, for example, a halogen atom, for example a chlorine, bromine or iodine atom. When R¹⁰ is directly attached to ring X, R¹⁰ may, for example, be a methylsulphinyl or methylsulphonyl radical. The process may be conducted in a diluent or solvent, for example t-butanol, and the reaction may be accelerated or completed by the application of heat, for example by heating to the boiling point of the diluent or solvent. When G is an oxygen or sulphur atom it is advantageous to conduct the reaction in the presence of a base. When the diluent or solvent is t-butanol, the base may be sodium t-butoxide.

(f) for those compounds in which R³ is a radical of the formula NHR⁴ in which R⁴ is a hydrogen atom, reaction of a compound of the formula XVI:

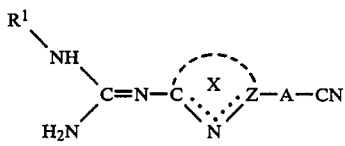

with a compound of the formula XVII:

The reaction may be conducted in a diluent or solvent, for example n-propanol or t-butanol, and may be accelerated or completed by the application of heat, for example by heating to the boiling point of the diluent or solvent.

(g) for those compounds in which Z is a nitrogen atom, reaction of a compound of the formula XVIII:

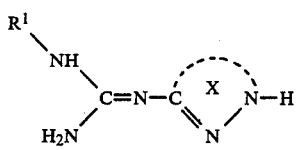   XVIII with a compound of the formula XIX:

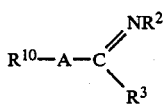   XIX in which $R^{10}$ is a displaceable radical. $R^{10}$ is, for example, a halogen atom, for example a chlorine, bromine or iodine atom.

(h) construction of the guanidine radical attached to ring X by reaction of the appropriate thiourea, or a 1-6C S-alkyl (e.g. S-methyl) or S-benzyl derivative thereof, or a salt of such a derivative, with the appropriate amine. The guanidine radical in the compound of the formula I contains three nitrogen atoms, each of which carries different substituents. The appropriate amine for use in this reaction may therefore be ammonia, an amine of the formula $R^1NH_2$ or an amine of the formula XX:

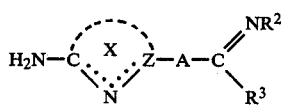   XX

The reaction may be conducted in a diluent or solvent such as methanol or ethanol. In many cases it is advantageous to use a catalyst such as lead oxide, mercuric oxide or sodium hypochlorite. The reaction may be conducted at ambient temperature or it may be accelerated or completed by the application of heat, for example by heating to the boiling point of the diluent or solvent.

(i) construction of the guanidine radical attached to ring X by reaction of the appropriate cyanamide with the appropriate amine. Since the guanidine radical in the compound of the formula I contains only one unsubstituted nitrogen atom there are two appropriate amines, namely the amine of the formula $R^1NH_2$ or of the formula XX given above.

(j) for those compounds in which $R^3$ is a radical of the formula $NHR^4$ in which $R^2$ and $R^4$ are joined to form a 1,2,4-triazole ring substituted in the 5-position by an amino or hydroxy radical, br a 1,3,5-triazine ring substituted in the 4-position by an amino or hydroxy radical and in the 6-position by a hydrogen atom or an alkyl, trifluoromethyl, aryl, arylalkyl, alkoxycarbonylalkyl, hydroxyalkyl, heteroarylalkyl, furyl, thienyl, pyrrolyl, thiazolyl, oxazolyl, imidazolyl, thiadiazolyl, oxadiazolyl, triazolyl, pyrazolyl, or pyrimidyl radical, reaction of a compound of the formula XXI:

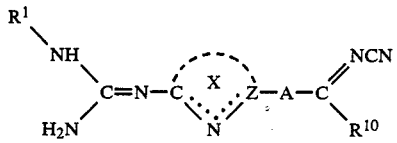   XXI in which $R^{10}$ is a displaceable radical with hydrazine or with a compound of the formula XXII:

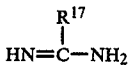   XXII respectively in which $R^{17}$ is a hydrogen atom or a 1-6C alkyl, trifluoromethyl, 6-10C aryl, 7-11C arylalkyl, 2-6C alkoxycarbonylalkyl, 1-6C hydroxyalkyl, heteroaryl-(1-6C)alkyl, furyl, thienyl, pyrrolyl, thiazolyl, oxazolyl, imidazolyl, thiadiazolyl, oxadiazolyl, triazolyl, pyrazolyl or pyrimidyl radical, whereafter, if desired, the amino radical on the 1,2,4-triazole or 1,3,5-triazine ring so formed is transformed to a hydroxy radical by standard methods. $R^{10}$ may, for example, be a 1-6C alkoxy radical, for example a methoxy radical. The subsequent transformation of amino radical to hydroxy radical may be carried out, for example, by hydrolysis or by diazotisation followed by hydrolysis.

(k) for those compounds in which ring X is a thiazole ring, reaction of a compound of the formula XXIII:

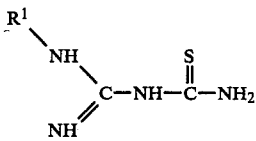   XXIII with a compound of the formula XXIV:

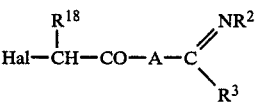   XXIV in which Hal is a chlorine or bromine atom and $R^{18}$ is a hydrogen atom or the optional substituent on the thiazole ring. The reaction may be conducted in a diluent or solvent such as acetone and may be accelerated or completed by the application of heat, for example by heating to the boiling point of the diluent or solvent.

When the process of the invention manufactures the compound of the formula I in the form of the free base and an acid-addition salt is required, the compound of the formula I in the free base form is reacted with an acid which affords a pharmaceutically-acceptable anion.

A critical intermediate for preparing the starting materials for several of the processes of the invention is the starting material of the formula XVI for use in process (f). This starting material may be prepared by separate construction of the two side chains on the appropriate ring X. Thus the left hand side chain may be constructed by reduction of a nitro group to an amino group, reaction of this amino group with an isothiocyanate of the formula $R^1N{=}C{=}S$. and finally reaction of the resulting thiourea with ammonia in the presence of mercuric oxide. The method of construction of the right hand side chain may vary depending on the nature of ring X, the nature of the atom in ring X to which A is attached (carbon or nitrogen) and the presence or absence of inserted atoms or groups in chain A. When A contains no inserted group, or the inserted group is a phenylene radical and Z is a carbon atom, it is preferable to construct ring X with the right hand side chain already in place. Thus, for example, when ring X is a pyrimidine ring, it may be formed by reaction of a suitably substituted amidine with 2-chloroacrylonitrile to give the corresponding 4-aminopyrimidine derivative. When the inserted group in A is a cycloalkylene radical, the chain A may be constructed by a conjugate addition to the corresponding cycloalk-2-enone. When the inserted group in A is a vinylene or ethynylene radical, A may be introduced by formation of the double or triple bond by standard coupling methods. When the inserted group in A is an oxygen or sulphur atom or an NH or N-alkyl radical, the right hand side chain may be built up by a method similar to that in process (e), for example as illustrated in Example 1. When Z is a nitrogen atom, the right hand chain may be formed by a method similar to that in process (g), for example as illustrated in Example 7.

The starting material of the formula V for use in process (a) in which $R^9$ is a hydrogen atom and $R^{10}$ is an alkoxy radical, or of the formula VII for use in process (b) in which $R^{10}$ is an alkoxy radical, may be prepared from the starting material of the formula XVI by treatment with anhydrous HCl in a diluent or solvent of the formula $R^{10}$—OH, for example as illustrated in Examples 1, 2, 7, 8 and 9.

The starting material of the formula XI for use in process (c) may be prepared from the starting material of the formula VII in which $R^{10}$ is a displaceable radical by reaction with a compound of the formula XXV:

$H_2NNHCOR^{16}$　　　　　　　　　　　XXV

. The starting material of the formula XII or XIII for use in process (e) and the starting material of the formula XIII for use in process (g) may be prepared by construction of the substituted guanidine radical on a suitably-substituted ring X.

The starting material of the formula XX for use in process (h) or (i) may be prepared by the methods described above for the preparation of compounds of the formula V or VII in which the right hand chain is constructed first, followed by use of one of the processes (a) or (b).

The cyanamide corresponding to the amine of the formula XX for use in process (i) may be prepared by reaction of the compound of the formula XX with cyanogen bromide.

The starting material of the formula XXI for use in process (j) may be prepared by reaction of the compound of the formula V in which $R^9$ is a hydrogen atom and the nitrogen to which it is attached is in the protonated form with cyanamide.

As noted above, the guanidine derivative of the invention is a histamine H-2 antagonist, inhibits the secretion of gastric acid in warm-blooded animals and is therefore useful in the treatment of peptic ulcers and other conditions caused or exacerbated by gastric acidity, including stress ulcers and gastrointestinal bleeding due to trauma.

The histamine H-2 antagonist activity may be demonstrated on standard tests, for example by the ability of the compound of the formula I to inhibit the histamine-induced uptake of aminopyrine into the acid space of parietal cells.

The test is carried out as follows:

Gastric mucosa from the New Zealand white rabbit is removed from the underlying muscle and washed in Buffer 1 [containing per liter NaCl; (8.007 g.), KCl (0.201 g.), $Na_2HPO_4$ (0.113 g.), $KH_2PO_4$ (0.204 g.), $CaCl_2.2H_2O$ (0.132 g.), $MgCl_2$ (0.101 g.) and glucose (1 g.), adjusted to pH 7.4 with NaOH]. The tissue is finely chopped, suspended in Buffer 1 and washed three times with Buffer 1. The tissue is then suspended in dispersion medium collagenase (Sigma Chemical Co., Type V; 100 mg.) and bovine serum albumin (Miles Laboratories Ltd., Fraction V; 100 mg.) in Buffer 1 (100 ml.); 50 ml. per 10 g. net weight of tissue]and incubated at 30° C. and pH 7.4 (maintained by continuous monitoring) with stirring under an oxygen atmosphere. After 30 minutes the tissue is allowed to settle and the supernatant liquid is removed. Fresh dispersion medium (50 ml. per 10 g. wet weight of tissue) is added and incubation is continued with the tissue being largely dispersed into glands and whole cells after 40-60 minutes. Any remaining large pieces of tissue are removed by filtration through nylon mesh. The mixture of glands and cells is collected by centrifugation at 200 x g. and suspended in Buffer 1 containing 1% bovine serum albumin (Miles Laboratories Ltd., Fraction V). Finally the cells and glands are washed 3 times with Buffer 1 and suspended in Buffer 2 [containing Eagles MEM (500 ml.), Aprotinin (Sigma Chemical Co., 10 mg.) and HEPES (2-[4-(2-hydroxyethyl)piperazin-1-yl]ethanesulphonic acid; 150 mM., 20 ml.) adjusted to pH 7.4 with NaOH; 150 ml. per 10 g. net weight of tissue]. The tissue suspension is stirred under an oxygen atmosphere at 32° C. for at least 1 hour before use. The tissue suspension is incubated with the test compound and aminopyrine (10 μM) labelled with $C^{14}$ on the dimethylamino group (0.1 μCi/ml.) for 20 minutes. The uptake of the aminopyrine is then stimulated by addition of histamine and the phosphodiesterase inhibitor ICI 63197 (*Biochem. Soc. Special Publication* 1, 1973, pp 127-132) to final concentrations of $10^{-5}$M. and $5 \times 10^{-7}$M respectively. After 18 minutes the cells/glands are separated from the incubation medium by filtration of the suspension through glass microfibre filters. The cells/glands are quickly ( <10 seconds) washed three times with ice-cold Buffer 1. The $C^{14}$ aminopyrine retained by the tissue is measured on a scintillation counter and the degree of inhibition of uptake by the test compound is calculated by reference to a control sample. The concentration of test compound giving 50% inhibition is then calculated graphically from a series of tests run at different concentrations.

All the compounds exemplified in this specification gave a 50% inhibition of uptake of aminopyrine at or below a concentration of 3 μM.

The inhibition of the secretion of gastric acid may be demonstrated in standard tests, for example by the ability of the compound of the formula I, when dosed intravenously, intragastrically or orally, to inhibit the secretion of acidic gastric juice in, for example, rats,or dogs provided with denervated fundic pouches, and whose gastric secretion is stimulated by administration of a secretagogue, for example histamine, pentagastrin, bethanechol or food.

The test in rats is carried out as follows:

Female rats (200–230 g.) are anesthetized by intramuscular administration of urethane (1.5 g/kg.) anc the trachea cannulated. A soft tuue is passed down tne oesophagus into the stom.ach and secured by a tie in the neck region. A multi-orifice plastic tube (3 mm. diameter) is passed into the antral region of the stomach, via an incision in the duodenum, and tied in place by means of a ligature around the pylorus. Saline (9 g./1. NaCl) is perfuseu through the stomach via the oesophageal cannula at a rate of 7 ml./minute and collected into beakers from the pyloric outlet over periods of 10 minutes. Acid secretion is stimulated by subcutaneous administration of the specific h-2 agonist dimaprit in a loading dose of 10 mg./kg. followed by an infusion of 30 mg./kg./hour. Acid output is computed by titration of the 10 minute samples to an end point of ph 6.4 with 20 mM. NaOH. When secretion has reached a plateau (three consecutive readings within 5%) the test compound is administered intravenously via a cannula placed in the left external jugular vein. Secretion is then measured for a further 2 hours. A stock solution of each test compound is prepared (10 mg./ml. in DMSO) and appropriate dilution made with saline to enable injection in a dose volume of 1 ml./kg. (DMSO <2%).

The test in dogs provided with denervated fundic pouches is carried out as follows:

Male beage dogs (14–22 kg.) are prepared with vagally denervated pouches of the fundic gland area by the method of Rudick et al. (*J. Surg. Res.* 1967, 7, 383). The animals are allowed 4–6 weeks to recover from surgery and a further period of 2–3 months prior to routine use, to allow for table training and standardization of secretory responses. The dogs are starved for 23 hours before use water ad lib) and during experiments they are lightly restrained in cloth slings. After rinsing the pouch with warm water, histamine is infused subcutaneously at a rate of 10 µg./minute. This dose of agonist produces a submaximal (60–90% of maximum) increase in acid output in all dogs used. Pouch secretions are collected over 15 minute periods into graduated glass test-tubes and the volume measured to the nearest 0.1 ml. A 500 µl sample is diluted with 5 ml. of saline and titrated to pH 7.0 with 100 mM.NaOH. Total acid output is computed from the product of acid concentration and volume of juice secreted. Compounds are administered intravenously (0.1 ml./kg.) via a cephalic vein or orally in a gelatin capsule when a secretory plateau (3 consecutive readings within 10%) has been attained. Secretion is measured for a period of 3 hours following administration of test compound.

The results obtained in the aminopyrine test are predictive of activity in the rat and dog tests.

No overt toxicity or side effects were noted during the rat or dog tests. The compounds N-cyano-5-(4-[2-propylguanidino]pyrimid-2-yl)valeramidino was administered intravenously to groups of two anaesthetised rats and four conscious mice at doses which were respectively ten times and one hundred times the dose, in mg./kg., which produced an approximate 50% inhibition of gastric secretion in the anaesthetised rat. No toxic symptoms were noted in any of the dosed animals.

A number of compounds exemplified in this specification exhibit inhibition of acid secretion which shows little or no decline from peak inhibition for several hours.

The N-methylcyanoguanidine group in known L-2 receptor antagonists is potentially changeable into the carcinogenic N-nitroso N-methylcyanoguanidine group in the mammalian body (Pool et al., *Toxicology,* 1979, 15, 69). The corresponding group in the compounds of the present invention, $C(R^3)=NR^2$, is resistant to reaction with nitrous acid over the pH range 1-4 (Baum et al., *J. Chem. Research* (S), 1980, 212-213) when $R^4$ is $NHR^7$ and $R^3$ and $R^7$ are joined to form a triazole, imidazole or 4-hydroxypyrimidine ring.

According to a further feature of the invention there is provided a pharmaceutical composition which comprises a guanidine derivative of the invention in association with a non-toxic pharmaceutically-acceptable diluent or carrier.

The pharmaceutical composition may, for example, be in a form suitable for oral, rectal, parenteral or topical administration, for which purposes it may be formulated by means known to the art into the form of, for example, tablets, capsules, aqueous or oily solutions or suspension, emulsions, dispersible powders, suppositories, sterile injectable aqueous or oily solutions or suspensions, gels, creams, ointments or lotions.

In addition to the guanidine derivative of the formula I, the pharmaceutical composition of the invention for oral, rectal or parenteral administration may also contain, or be co-administered with, one or more known drugs selected from antacids, for example aluminium hydroxide - magnesium hydroxide mixtures; antipepsin compounds, for example pepstatin; other histamine H-2 antagonists, for example cimetidine or ranitidine, ulcer healing agents, for example carbenoxolone or bismuth salts; anti-inflammatory agents, for example ibuprofen, indomethacin, naproxen or aspirin, prostaglandins, for example 16,16-dimethylprostaglandin $E_2$; classical antihistamines histamine H-1 antagonists), for example m.epyramine or diphenhydramine; anticholinergic agents, for example atropine or propantheline bromide; anxiolytic agents, for example diazepam, chlordiazepoxide or phenobarbital.

The pharmaceutical composition of the invention for topical administration may also contain, in addition to the guanidine derivative, one or more classical anti-histamines (histamine H-1 antagonists), for example mepyramine or diphenhydramine and/or one or more steroidal anti-inflammatory agents, for example fluocinolone or triamcinolone.

A topical formulation may contain 1–10% w/w of the guanidine derivative of the invention. A preferred pharmaceutical composition of the invention is one suitable for oral administration in unit dosage form, for example a tablet or capsule which contains between 15 mg. and 500 mg. of the guanidine derivative, or one suitable for intravenous, subcutaneous or intramuscular injection, for example a sterile injectable containing between 0.1% and 10% w/w of the guanidine derivative.

The pharmaceutical composition of the invention will normally be administered to man for the treatment of peptic ulcers and other conditions caused or exacerbated by gastric acidity in the same general manner as that employed for cimetidine, due allowance being made in terms of dose levels for the potency and duration of action of the guanidine derivative of the present invention relative to cimetidine. Thus each patient will receive an oral dose of between15 mg. and 1500 mg., and preferably between 20 mg. and 200 mg. of guanidine derivative or an intravenous, subcutaneous or intramuscular dose of between 1.5 mg. and 150 mg., and preferably between 5 mg. and 20 mg. of the guanidine derivative, the composition being administered 1 to 4 times per day. The rectal dose will be approximately the same as the oral dose. The composition may be administered less frequently when it contains an amount of guanidine derivative which is a multiple of the amount which is effective when given 1–4 times per day.

The invention is illustrated, but not limited, by the following Examples. The n.m.r. spectra are quoted in δ relative to tetramethylsilane (δ=O) as internal standard (s=singlet, d=doublet, t=triplet, q=quartet, m=multiplet, br=broad). The temperatures are in degrees Centigrade. The following contractions are used:
HOAc=acetic acid
DMF=dimethyl formamide
ether=diethyl ether
DMSO=dimethylsulphoxide
MeOH=methanol
EtOH=ethanol
THF=tetrahydrofuran
EtOAc=ethyl acetate Attention is drawn to the fact that 4-nitrotriazole (Example 7) is an explosion hazard.

EXAMPLE 1

To a mixture of 4-(4-[2-propylguanidino]pyrimid-2-ylthio)butyronitrile (0.8 g.) in MeOH (7 ml.) and CHCl$_3$ (7 ml.) at 0° was added dry HCl gas until the mixture was saturated. The resulting solution was allowed to stand at 0° for 2.5 days and then evaporated to dryness. To the residue of the imino-ether was added potassium carbonate (anhydrous, 4 g.) and water (10 ml.). The resulting mixture was extracted with CHCl$_3$ (3×20 ml.) and the CHCl$_3$ extracts washed with water (5 ml.), dried over magnesium sulphate, filtered and evaporated to dryness to give a crude sample of the imino-ether (0.60 g.). Without further purification the imino-ether (0.30 g.) was added to a mixture of cyanamide (0.04 g.) and MeOH (5 ml.) and the mixture stirred at room temperature for 2.5 hours, then evaporated to dryness. The residue was triturated with MeOH (5 ml.) and filtered to give N-cyano-4-(4-[2 propylguanidino]-pyrimid-2-ylthio)butanamidine (0.23 g.) as a white crystalline solid, m.p. 210°–215°.

The starting material may be obtained as follows:

4-Chlorobutyronitrile (0.23 g.) in EtOH (2 ml.) was added to a solution of 2-thiocytosine (0.25 g.) in 0.5N aqueous NaOH (5 ml.) and the mixture stirred for 18 hours. A further portion of 4-chlorobutyronitrile (0.23 g.) was added and the mixture stirred a further 24 hours. The solution was concentrated in vacuo to 2 ml. and cooled and the crystalline precipitate collected to give 4-[4-aminopyrimid-2-ylthio]butyronitrile (0.3 g.), m.p. 99°–100°.

A mixture of 4-[4-aminopyrimid-2-ylthio]butyronitrile (0.75 g.), propylisothiocyanate (0.8 g.) and pyridine (5 ml.) was heated at 130° for 2 hours and then heated under reflux for 18 hours. The solvent was removed by evaporation in vacuo and the residual oil was purified by medium pressure chromatography on silica using CHCl$_3$/MeOH 9.75:0.25 v/v as eluant. A portion of the purified product (0.3 g.) and EtOH (5 ml.) was added to EtOH saturated with ammonia (10 ml.) and mercuric oxide (0.22 g.). After 15 minutes the reaction mixture was filtered through diatomaceous earth and the filtrate was evaporated to give a white semi-crystalline solid which was purified by medium pressure chromatography on silica using CHCl$_3$/MeOH/aqueous ammonia (s.g. 0.880) 9:1:0.1 v/v/v as eluant. There was thus obtained 4-(4-[2-propylguanidine pyrimid-2-ylthio)-butyronitrile (0.18 g.) which was used without further purification.

EXAMPLE 2

To a mixture of 5-(4-[2 propylguanidino]pyrimid-2-yl)valeronitrile (0.60 g.) in MeOH (5 ml.) and CHCl$_3$ (5 ml.) at 0° was added dry HCl gas until the mixture was saturated. The resulting solution was allowed to stand at Oo for 2.5 days and then evaporated to dryness. The residue was taken up in a mixture of anhydrous potassium carbonate (3 g.) and water (10 ml.) and extracted with CHCl$_3$ (3×15 ml.). The CHCl$_3$ extracts were combined, washed with water (5 ml.) dried over magnesium sulphate, filtered and evaporated to dryness. To the residual imino-ether (0.25 g.) was added MeOH (5 ml.) and cyanamide (0.04 g.) and the mixture was stirred at room temperature for 3 hours, then evaporated to dryness and the residue purified by medium pressure (20–40 lb/in$^2$) liquid chromatography on silica using CHCl$_3$/MeOH/aqueous ammonia (s.g. 0.880) 9:1:0.1 v/v/v as eluant to give N-cyano-5-(4-[2-n-propylguanidino]pyrimid-2-yl-valeramidine (0.20 g.) as a white cyrstalline solid, m.p. 202°–205°.

The starting material may be prepared as follows:

A mixture of 2-(4-cyanobutyl)-4-aminopyrimidine (1.2 g.) and propylisothiocyanate (0.9 g.) was heated under reflux in pyridine (3 ml.) for 22 hours. The mixture was then evaporated to dryness and the residue purified by medium pressure chromatography using CHCl$_3$/MeOH/aqueous ammonia (s.g. 0.880) 19:1:0.05 v/v/v as eluant. The appropriate fraction was evaporated to dryness and the residue treated in concentrated ethanolic ammonia with mercuric oxide (2.2 g.). After 1 hour the mixture was filtered and the filtrate evaporated to dryness. Recrystallisation of the residue from acetone/petroleum ether (b.p. 60°–80°) gave 0.8 g. of 5-(4-[2-propylguanidino]pyrimid-2-yl)valeronitrile which was used without further purification.

EXAMPLE 3

To a solution of 1-imino-1-methoxy-4-(4-[2-propylguanidino)pyrimid-2-ylthio)butane (0.41 g.) in MeOH (8 ml.) was added acethydrazide (0.136 g.) in one portion. The reaction mixture was stirred at room temperature for 3 hours and the solution was evaporated to dryness. The residue was triturated with ether and acetonitrile to give N-acetyl-4-(4-[2-propylguanidino]-pyrimid-2-ylthio)butyramidrazone as a white solid (0.307 g.), m.p. 179°–181°.

EXAMPLE 4

N-Acetyl-4-(4-[2-n-propylguanidino]pyrimid-2-ylthio)butyramidrazone (0.25 g.) was heated in an oil bath at 190° for 10 minutes. The resulting glass was purified by medium pressure chromatography using EtOAc/MeOH/aqueous ammonia (s.g. 0.880) 6:1:0.5 v/v/v as eluant. The main peak was dissolved in acetone and added to an acetone solution of maleic acid (0.15 g.). The precipitate was collected and washed with acetone to give 5-methyl-3-(3-[4-(2-propylguanidino)pyrimid-2-ylthio]propyl-1,2,4-triazole dimaleate (0.(825 g.), m.p. 150°–153°.

EXAMPLE 5

A mixture of 5-(4-[2-propylguanidino]pyrimid-2-yl)valeramidine hydrochloride (0.4 g.) and the sodium salt of ethyl 2-formylbutyrate (1.5 g.) in MeOH (5 ml.) was heated under reflux for 4 hours. The solvent was evaporated in vacuo and the residue was partitioned between water (pH 7) and EtOAc. The EtOAc layer was separated, dried (MgSO$_4$) and evaporated in vacuo to give 2-[4-(4-(2-propylguanidino]pyrimid-2-yl)butyl]-5-ethyl-4-hydroxypyrimidine as an oil (0.13 g.) which was characterised by conversion to the bis hydrogen maleate salt (0.11 g.), m.p. 140°–142°.

The starting material may be prepared as follows:

A mixture of methyl 5-(4-[2-propylguanidino]pyrimid-2-yl)valerimidate (0.4 g.) and ammonium chloride (0.076 g.) in MeOH (20 ml.) was stirred at ambient temperature for 1 hour and the solvent evaporated in vacuo to give 5-(4-[2-propylguanidino]pyrimid-2-yl)valeramidine hydrochloride (0.4 g.) as an oil which was used without further purification.

EXAMPLE 6

The process of Example 5 was repeated using ethyl 2-formylpropionate in place of ethyl 2-formylbutyrate to give 2-[4-[4-[2-propylguanidino]pyrimid2-yl)butyl]-5-methyl-4-hydroxypyrimidine, m.p. 213°–215° (yield 15%).

EXAMPLE 7

Crude N-acetylamino-5-[4-(2-methylguanidino)1,2,3-triazol-2-yl]valeramidine (0.54 g.) in EtOH (15 ml.) was heated under reflux for 18 hours. The solvent was evaporated and the residue converted to the maleate salt in acetone to give 3-methyl-5-(4-[4-(2-methylguanidino)-1,2,3-triazol-2-yl]butyl)-1,2,4-triazole dihydrogen maleate as a white solid (0.454 g.), m.p. 143°–145° (yield 49%).

The starting material may be prepared as folllows:

A stirred solution of 4-nitro-1,2,3-triazole (23.0 g.) in dry DMF (135 ml.) was treated at room temperature with a dispersion of sodium hydride [4.8 g.) in mineral oil (4.8 g.). The mixture was stirred for 30 minutes then treated with 5-bromovaleronitrile (33.0 g.). The mixture was stirred overnight at room temperature then poured into water. The product was extracted into EtOAc and purified by column chromatography on silica gel (1 kg.) eluted with EtOAc/petroleum ether (b.p. 60°–80°) 1:1 v/v to give 22.3 g. of 5-(4-nitro-1,2,3-triazol-2-yl)valeronitrile as an oil.

A suspension of palladium on charcoal (5% w/w; 0.5 g.) in a solution of 5-(4-nitro-1,2,3-triazol-2-yl)valeronitrile (1.0 g.) in HOAc (20 ml.) was stirred under one atmosphere of hydrogen until 420 ml. of hydrogen had been absorbed. The mixture was filtered and evaporated to give 0.85 g. of 5-(4-amino-1,2,3-triazol-2-yl)valeronitrile as an oil.

A solution of 5-(4-amino-1,2,3-triazol-2-yl)valeronitrile (1.65 g.) in acetonitrile (5 ml.) and methylisothiocyanate (0.73 g.) was stirred for 18 hours at ambient temperature and then heated under reflux for 6 hours. The solvent was evaporated and the residue was triturated with ether/EtOH to give 5-[4-(3-methylthioureido)-1,2,3-triazol-2-yl]valeronitrile as a white solid.

A solution of 5-[4-(3-methylthioureido)1,2,3-triazol-2-yl]valeronitrile in methanolic ammonia (6M; 15 ml.) was treated with mercuric oxide (1.1 g.) and tne mLxture stirred for 3 hours at room temperature. The resulting suspension was filtered through diatomaceous earth and the filtrate evaporated to give 5-[4-(2-methylguanidino)-1,2,3-triazol-2-yl]valeronitrile as a yellow oil.

A solution of 5-[4-(2-methylguanidino)-1,2,3-triazol-2-yl]valeronitrile (0.8 g.) in a mixture of chloroform (15 ml.) and MeOH (5 ml.) was saturated at 0° with hydrogen chloride gas and the mixture maintained at 0° for 3 days. The mixture was evaporated to dryness and the residue basified with cold sodium carbonate solution and extracted witn chloroform. The extract was dried and evaporated to give methyl 5-[4-(2-methylguanidinb)1,2,3-triazol-2-yl]valerimidate as a yellow oil (1.07 g.).

Methyl 5-[4-[2-methylguanidino)-1,2,3-triazol2-yl]valerimidate (1.0 g.) in MeOH (12 ml.) was treated with acethydrazide (0.22 g.) and the solution stirred for 18 nours. Evaporation of the solvent and trituration of the resioue with ether/EtOH gave N-acetylamino-5[4-(2-methylguanidino)-1,2,3-triazol-2-yl]valeramidine as a yellow sticky solid [0.54 g.) which was used without further purification.

EXAMPLE 8

Crude methyl 5-(4-guanidino-1,2,3-triazol-2-yl)valerimidate hydrochloride (0.42 g.) in MeOH (8 ml.) was treated with triethylamine (0.35 g.) followed after 0.5 hours by acethydrazide (0.13 g.). After a further 0.5 hours the solution was heated under reflux for 6 hours then evaporated to dryness. The residue was purified by medium pressure chromatography using chloroform/MeOH/aqueous ammonia (s.g. 0.880) 8:2:0.1 v/v/v as eluant to give a gum which was converted to the fumarate in MeOH. The solid was filtered and washed with warm MeOH to give 3-methyl-5-[4-(4-guanidino-1,2,3-triazol-2-yl)butyl]-1,2,4-triazole fumarate (yield 19%) having the following n.m.r. in d$_6$DMSO:- 1.4–2.1 (m, 4H); 2.15 (s, 3H); 2.61 (t, 2H); 4.4 (t, 2H); 6.68 (s, 1H); 7.08 (s, 1H); 7.26 (br s, 4H).

The starting material may be prepared as follows:

A solution 5-(4-amino-1,2,3-triazol-2-yl)valeronitrile hydrochloride (2.01 g.) in EtOH (15 ml.) was treated with cyanamide (0.42 g.) and the solution heated under reflux for 4.5 hours. A further 0.1 g. of cyanamide was added and heating under reflux was continued for 2 hours. The solution was evaporated and the residue basified with ammonia and continuously extracted for 24 hours with EtOAc to give a yellow oil which was purified by medium pressure chromatography using chloroform/MeOH/aqueous ammonia (s.g. 0.880) 8:2:0.1 v/v/v as eluant to give 5-(4-guanidino-1,2,3-triazol-2-yl)valeronitrile as a colourless oil (0.45 g.).

A solution of 5-(4-guanidino-1,2,3-triazol-2-yl)valeronitrile (0.41 g.) in chloroform (15 ml.) and MeOH (4 ml.) was saturated at 0° with gaseous hydrogen chloride and the solution kept at 0° for 3 days. Lvaporation gave methyl 5-(4-guanidino-1,2,3-triazol-2-yl)valerimidate hydrochloride which was used without further purification.

EXAMPLE 9

A solution of methyl 5-[4-(2-ethylguanidino)-1,2,3-triazol-2-yl]valerimidate (1.57 g.) in MeOH (6 ml.) was treated with acethydrazide (0.42 g.) and the solution allowed to stand for 18 hours. Evaporation gave a brown gum which was triturated with ether/EtOH to give N-acetylamino-4-[4-(2-ethylguanidino)-1,2,3-triazol-2-yl]valeramidine as a white solid (1.1 g.), m.p. 136°–138° (yield 60%).

The starting material may be prepared as follows:

A solution of 5-(4-amino-1,2,3-triazol-2-yl)valeronitrile (1.65 g.) in acetonitrile (6 ml.) was treated with ethylisothiocyanate (0.87 g.) and the solution stirred for 2.5 days then heated under reflux for 4.5 hours. Evaporation of the solvent gave 5-[4-(3-ethylthioureido)-1,2,3-triazol-2-yl]valeronitrile.

A solution of 5-[4-(3-ethylthioureido)-1,2,3-triazol-2-yl]valeronitrile (2.2 g.) in methanolic ammonia (6M; 20 ml.) was treated with yellow mercuric oxide (2.08 g.) and the resulting suspension stirred at room temperature for 18 hours. The suspension was filtered through diatomaceous earth and the filtrate evaporated to give an oil which was purified by medium pressure chromatography using EtOAc then MeOH/EtOAc 1:1 v/v as eluants to give 5-[4-[2-ethylguanidino)-1,2,3-triazol-2-yl]valeronitrile (1.35 g.).

A solution of 5-[4-[2-ethylguanidino)-1,2,3-triazol-2-yl]valeronitrile (1.35 g.) in MeOH (5 ml.) and chloroform (20 ml.) was saturated with gaseous HCl at 0° and the solution kept at 0° for 2.5 days. Evaporation of the solvent gave an oil which was basified with cold potassium carbonate solution and then extracted with chloroform to give methyl 5-[4-(2-ethylguanidino)1,2,3-triazol-2-yl]valerimidate (1.57 g.) which was used without further purification.

EXAMPLE 10

The process of Example 7 was repeated using the product of Example 9 as starting material to give 3-methyl-5-(4-[4-(2-ethylguanidino)-1,2,3-triazol-2-yl]butyl)-1,2,4-triazole maleate, m.p. 129°-132° (yield 50%).

EXAMPLE 11

A tablet containing 200 mg. of N-cyano-4-(4-[2-propylguanidino]pyrimid-2-ylthio)butanamidine may be prepared using ingredients in the following proportions:

|  | mg./tablet |
|---|---|
| (a) Tablet Core |  |
| Active agent | 200 |
| Lactose | 68.5 |
| Calcium carboxymethylcellulose | 22.5 |
| Polyvinylpyrrolidone | 6.0 |
| Magnesium stearate | 3.0 |
| (b) Tablet Coat |  |
| Hydroxypropylmethylcellulose | 4.5 |
| Polyethylene glycol | 0.9 |
| Titanium dioxide | 1.35 |

The active agent, lactose and calcium carboxymethylcellulose are mixed. An aqueous solution of polyvinylpyrrolidone is added, and the mass is then mixed until it is suitable for granulation. The mass is then granulated and dried. The magnesium stearate is blended with the dried granules and the resulting mixture is compressed into tablets. The tablets are film-coated using an aquous or solvent suspension of hydroxypropylmethylcellulose, polyethylene glycol and titanium dioxide.

We claim:

1. A guanidine derivative of the formula I:

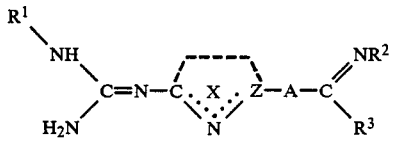

in which $R^1$ is hydrogen, 1-10C alkyl, 3-8C cycloalkyl, 4-14C cycloalkylaklyl, 3-6C alkenyl, 3-6C alkynyl, 1-6C alkanoyl, phenyl, 7-11C phenylalkyl or benzoyl, the phenyl, phenylalkyl and benzoyl being optionally substituted on the phenyl ring by one or two substituents selected from halogen, 1-6C alkyl, 1-6C alkoxy, 1-6C alkylthio, trifluoromethyl, hydroxy and amino;

in ring X the dotted line is a double bond on one side of the nitrogen and Z is carbon or nitrogen such that ring X is pyrazine, pyridine, pyrimidine or 1,3,5-triazine, which ring may, where possible, carry one or two optional substituents, the optional substituents on ring X being selected from fluorine, chlorine, bromine, 1-6C alkyl, 1-6C alkoxy, trifluoromethyl, hydroxy and amino;

—A— is phenylene, 5-7C cycloalkylene, or a 1-8C alkylene chain which is optionally substituted by one or two 1-3C alkyls and into which is optionally inserted, as part of the backbone of the chain, one or two groups selected from oxygen, sulphur, NH, 1-6C N-alkyl, cis and trans vinylene, ethynylene, phenylene and 5-7C cycloalkylene, provided that the shortest link between ring X and $C(R^3)=NR^2$ is of at least 3 atoms, provided that when an optional insertion is made in chain A which results in the inserted group being directly attached to $C(R^3)=NR^2$ the inserted group is other than NH or N-alkyl, and provided that no two insertions selected from oxygen, sulphur, NH and N-alkyl are directly attached one to the other;

$R^2$ is hydrogen, 1-6C alkyl, 3-8C cycloalkyl, 4-14C cycloalkylalkyl, 1-6C haloalkyl, 1-6C hydroxyalkyl, 1-6C aminoalkyl, 2-10C alkylaminoalkyl, 3-14C dialkylaminoalkyl, 2-6C carboxyalkyl, 1-6C alkanoyl, benzoyl, phenyl, 7-11C phenylalkyl, 2-6C alkenyl, 2-6C alkynyl, 2-6C haloalkanoyl, 1-6C thioalkanoyl, thiobenzoyl, cyano, carbamoyl, thiocarbamoyl, 2-6C alkylcarbamoyl, 3-10C dialkylcarbamoyl, 2-6C alkylthiocarbamoyl, 3-10C dialkylthiocarbamoyl, carboxyl, 2-6C alkoxycarbonyl, 2-6C alkoxythiocarbonyl oxamoyl, sulphamoyl, 1-6C alkylsulphamoyl, 2-10C dialkylsulphamoyl, phenylsulphamoyl, 7-11C phenylalkylsulphamoyl, 1-6C alkanesulphonyl, benzenesulphonyl, hydroxy, 1-6C alkoxy, amino, 1-6C alkylamino, 2-10C dialkylamino, phenylamino, 2-6C alkoxycarbonylamino, phenylcarbonylamino, 1-6C alkanoylamino, benzoylamino, 1-6C thioalkanoylamino, thiobenzoylamino, heteroarylcarbonylam heteroaryl-(1-6C)alkylcarbonylamino, 1-6C alkanesulphonylamino, benzenesulphonylamino, ureido, thioureido, oxamoylamino, heteroaryl or heteroaryl-(1-6C)alkyl;

$R^3$ is of the formula $HNR^4$ in which $R^4$ is hydrogen, 1-6C alkyl, 2-6C alkenyl, 2-6C alkynyl, cyano, 1-6C alkanoyl, carbamoyl, 2-6C alkylcarbamoyl or 1-6C alkanoylamino;

or $R^2$ is a hydrogen, 1-6C alkyl, 2-6C alkenyl or 2-6C alkynyl and $R^3$ is carboxy;

and wherein when $R^2$ is or contains heteroaryl that heteroaryl is pyridyl or pyrimidyl each of which is optionally substituted by one or two substituents selected from methyl and amino;

and the pharmaceutically-acceptable acid-addition salts thereof.

2. A guanidine derivative of the formula I given in claim 1 in which $R^1$ is hydrogen, methyl, ethyl, propyl, isopropyl, butyl, cyclohexyl, cyclohexylmethyl, allyl, propargyl, acetyl, phenyl, benzyl or benzoyl, the phenyl, benzyl and benzoyls being optionally substituted on the benzene ring by one or two substituents selected from fluorine, chlorine, bromine, methyl, methoxy, methylthio, trifluoromethyl, hydroxy and amino; the optional substituents on ring X are selected from fluorine, chlorine, bromine, methyl, methoxy, trifluoromethyl, hydroxy and amino;

—A— is phenylene, cyclopentylene, cyclohexylene, trimethylene, tetramethylene, pentamethylene, thioethylene, thiotrimethylene, thiotetramethylene, thiopentamethylene, oxyethylene, oxytrimethylene, oxytetramethylene, methylenethiomethylene, methylenethioethylene, methylenethiopropylene, methyleneoxymethylene, methyleneoxyethylene, ethyleneoxyethylene, oxy-2-methylethylene, thiopropylenethiomethylene, oxypropyleneoxy, oxyethyleneoxymethylene, oxyethylenethio, oxypropylenethio, iminoethylene, iminopropylene, vinylenepropylene, oxymethylenevinylene, 1,3-phenylene, 1,3-cyclopentylene, methylene-1,4-phenylene, ethyleneoxymethylene-1,4-phenylene, oxy-1,3-phenylenemethylene or thiomethyleneethynylenemethylene;

$R^2$ is hydrogen, methyl, cyclohexyl, cyclobutylmethyl, 2,2,2-trifluoroethyl, 2-hydroxyethyl, 2-aminoethyl, 2-methylaminoethyl, 2-dimethylaminoethyl, 2-carboxyethyl, acetyl, benzoyl, phenyl, benzyl, allyl, propargyl, trifluoroacetyl, thioacetyl, thiobenzoyl, cyano, carbamoyl, thiocarbamoyl, methylcarbamoyl, dimethylcarbamoyl, methylthiocarbamoyl, dimethylthiocarbamoyl, carboxy, methoxycarbonyl, methoxythiocarbonyl, oxamoyl, sulphamoyl, methylsulphanoyl, dimethylsulphamoyl, phenylsulphamoyl, benzylsulphamoyl, methanesulphonyl, benzenesulphomoyl, hydroxy, methoxy, amino, methylamino, dimethylamino, phenylamino, methoxycarbonylamino, phenoxycarbonylamino, acetylamino, benzoylamino, thioacetylamino, thiobenzoylamino, heteroarylcarbonylamino, heteroarylacetamino, methanesulphonylamino, benzenesulphonylamino, ureido, thioureido, oxamoylamino, heteroaryl or heteroarylmethyl;

$R^3$ is of the formula $NHR^4$ in which $R^4$ is hydrogen, methyl, allyl, propargyl, cyano, acetyl, carbamoyl, methylcarbamoyl or acetyl - amino;

or $R^2$ is hydrogen, methyl, allyl or propargyl and $R^3$ is carboxy;

and wherein when $R^2$ is or contains heteroaryl that heteroaryl is pyridyl or pyrimidyl, such radical being optionally substituted by one or two substituents selected from methyl and amino;

and the pharmaceutically-acceptable acid-addition salts thereof.

3. A guanidine derivative as claimed in claim 2 in which $R^2$ is cyano and $R^3$ is of the formula $NHR^4$ in which $R^4$ is hydrogen.

4. A guanidine derivative as claimed in claim 3 in which $R^1$ is methyl or propyl.

5. A guanidine derivative as claimed in claim 4 in which ring X is pyrimidine in which A is linked at the 2-position and the ring carries no optional substituent.

6. A guanidine derivative as claimed in claim 5 in which —A— is a tetramethylene or thiotrimethylene.

7. A guanidine derivative selected from the group consisting of N-cyano-4-(4-[2-propylguanidino]pyrimid-2-ylthio)butanamidine, N-cyano-5-(4-[2-propylguandino]-pyrimid-2-yl)valeramidine, and the pharmaceutically-acceptable acid-addition salts thereof.

8. A guanidine derivative according to claim 1, said derivative being N-cyano-4-(4-[2-propylguanidino]-pyrimid-2-ylthio)butana 9. A guanidine derivative of the formula I:

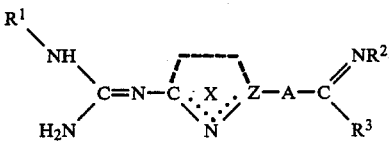

in which
$R^1$ is hydrogen, or 1-10C alkyl;
in which X the dotted line is a double bond on one side of the nitrogen and Z is carbon such that ring X is pyrimidine;
—A— is thiotrimethylene or tetramethylene;
$R^2$ is hydrogen, 1-6C alkanoylamino or cyano and $R^3$ is of the formula $NHR^4$ in which $R^4$ is hydrogen;
and the pharmaceutically-acceptable acid-addition salts thereof.

10. A guanidine derivative as claimed in claim 9 in which $R^1$ is hydrogen, methyl, ethyl or n-propyl and $R^2$ is hydrogen, cyano or acetylamino.

11. A guanidine derivative as claimed in claim 10 in which $R^1$ is methyl or propyl.

12. A guanidine derivative as claimed in claim 11 in which A is linked at the 2-position of the pyrimidine ring.

13. A guanidine derivative selected from the group consisting of N-cyano-4-(4-[2-propylguanidino]pyrimid-2-ylthio)butanamidine, N-cyano-5-(4-[2-n-propylguandino]pyrimid-2-yl)valeramidine, N-acetyl-4-(4-[2-propylguanidino]pyrimid-2-ylthio)butyramidrazone, 5-(4-[2-propylguanidino]pyrimid-2-yl)valeramidine and the pharmaceutically-aceptable acid-addition salts thereof.

14. A pharmaceutical composition which comprises a guanidine derivative as claimed in claim 1 in an amount sufficient to inhibit gastric acid secretion in a warm-blooded animal and in association with a pharmaceutically-acceptable diluent or carrier.

15. A pharmaceutical composition which comprises a guanidine derivative as claimed in claim 9 in an amount sufficient to inhibit gastric acid secretion in a warm-blooded animal and in association with a pharmaceutically-acceptable diluent or carrier.

16. A method of inhibiting gastric acid secretion in a warm-blooded animal comprising administering to the animal an effective amount of a compound of claim 1.

17. A method of inhibiting gastric acid secretion in a warm-blooded animal comprising administering to the animal an effective amount of a compound of claim 9.

* * * * *